(12) United States Patent
Inoue et al.

(10) Patent No.: US 8,795,957 B2
(45) Date of Patent: Aug. 5, 2014

(54) BLOOD COLLECTION CONTAINER

(75) Inventors: Tomonori Inoue, Shunan (JP); Yuuji Setoguchi, Shunan (JP); Ryusuke Okamoto, Shunan (JP); Katsuya Togawa, Tokyo (JP)

(73) Assignee: Sekisui Medical Co., Ltd., Tokyo (JP)

( * ) Notice: Subject to any disclaimer, the term of this patent is extended or adjusted under 35 U.S.C. 154(b) by 197 days.

(21) Appl. No.: 13/033,120

(22) Filed: Feb. 23, 2011

(65) Prior Publication Data

US 2011/0144536 A1    Jun. 16, 2011

Related U.S. Application Data

(63) Continuation of application No. PCT/JP2009/064947, filed on Aug. 27, 2009.

(30) Foreign Application Priority Data

Aug. 28, 2008    (JP) .................................. 2008-220029

(51) Int. Cl.
*A01N 1/02*    (2006.01)
(52) U.S. Cl.
USPC .......................... 435/2; 435/283.1; 435/288.1
(58) Field of Classification Search
None
See application file for complete search history.

(56) References Cited

U.S. PATENT DOCUMENTS

| 5,257,633 A * | 11/1993 | Vogler et al. .................. 600/576 |
| 6,686,204 B2 * | 2/2004 | Dubrowny et al. ............. 436/69 |
| 2005/0106071 A1 | 5/2005 | Minamoto et al. |
| 2008/0274532 A1 | 11/2008 | Minamoto et al. |
| 2008/0274540 A1 | 11/2008 | Minamoto et al. |

FOREIGN PATENT DOCUMENTS

| CN | 1656377 A | 8/2005 |
| EP | 1 508 804 A1 | 2/2005 |
| JP | 63-68138 A | 3/1988 |
| JP | 10-260180 A | 9/1998 |
| JP | 2001-269328 A | 10/2001 |
| JP | 2002-267660 A | 9/2002 |
| JP | 2002-323488 A | 11/2002 |
| JP | 2004-49894 A | 2/2004 |
| JP | 2004-148194 A | 5/2004 |
| JP | 2007-248175 A | 9/2007 |
| WO | WO-03/100414 A1 | 12/2003 |
| WO | WO-2006/098350 A1 | 9/2006 |

OTHER PUBLICATIONS

International Preliminary Report on Patentability for Application No. PCT/JP2009/064947 mailed Apr. 21, 2011.
International Search Report for Application No. PCT/JP2009/064947 mailed Nov. 2, 2009.

(Continued)

*Primary Examiner* — Blaine Lankford
*Assistant Examiner* — Thomas J Visone
(74) *Attorney, Agent, or Firm* — Cheng Law Group, PLLC

(57) ABSTRACT

The present invention provides a blood collection container capable of allowing blood to coagulate in a short time and preventing blood from coagulating with bubbles contained therein and thus preventing formation of bubbly clots when used to collect blood therein. A blood collection container 1 stores a blood coagulation promoting agent 4 for promoting blood coagulation and an antifoaming agent 5, which is a polyoxyalkylene or a derivative thereof. The amount of the antifoaming agent 5 is $2.0 \times 10^{-3}$ to 0.2 mg per mL of blood to be collected in the blood collection container 1.

18 Claims, 1 Drawing Sheet

(56) References Cited

OTHER PUBLICATIONS

Canadian Office Action for the Application No. 2,734,711 from Canadian Intellectual Property Office dated Oct. 11, 2011.

The First Office Action for Application No. 200980133105.1 from The State Intellectual Property Office of the People's Republic of China dated Jan. 4, 2012.

* cited by examiner

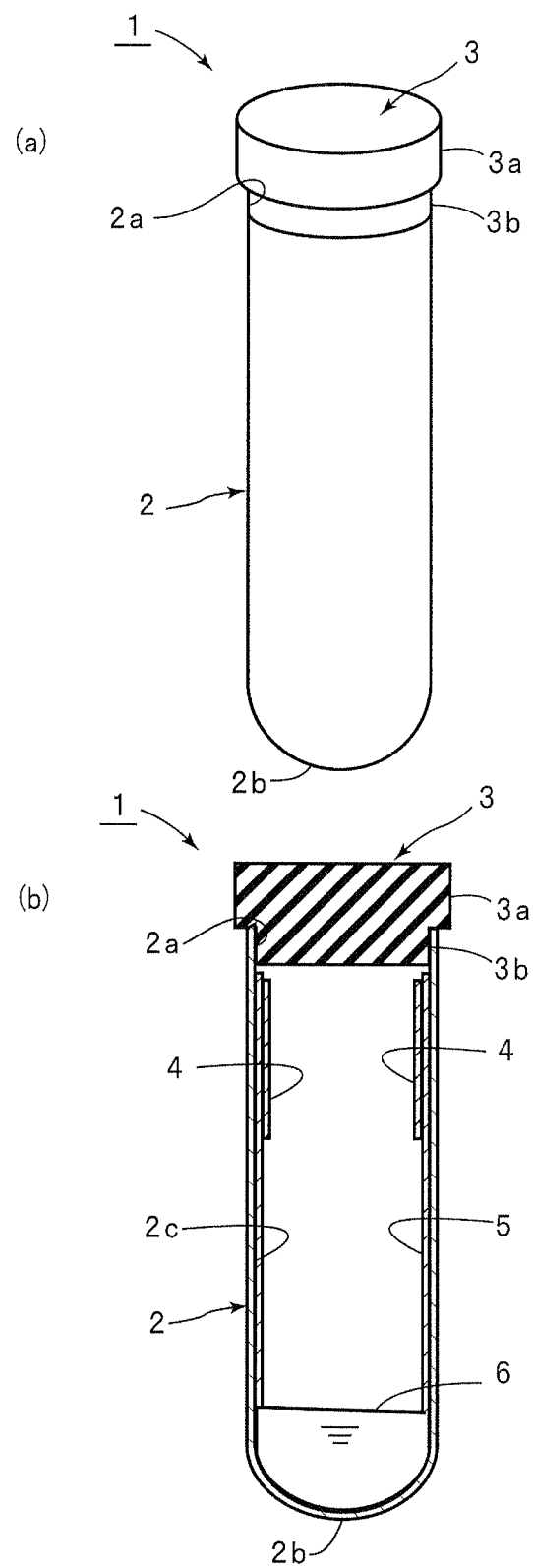

BLOOD COLLECTION CONTAINER

CROSS-REFERENCE TO RELATED APPLICATION

This application is a Continuation Application of International Application No. PCT/JP2009/064947, filed on Aug. 27, 2009, which claims priority to Japanese Patent Application No. 2008-220029 filed on Aug. 28, 2008, the entire contents of which are hereby incorporated by reference.

TECHNICAL FIELD

The present invention relates to a blood collection container for applications such as clinical examinations including serum biochemical analysis and serum immunological analysis.

BACKGROUND ART

Blood tests are commonly performed tests for prevention or diagnosis of diseases. In most cases, blood tests are performed for serum analysis such as serum biochemistry analysis, serum immunological analysis, serum hormone analysis, serum tumor marker analysis, and serum drug level analysis.

In order to collect serum from blood for serum analysis, blood collection containers such as vacuum blood collection tubes and blood collection tubes have been widely used. Serum is collected as follows: collecting blood in a blood collection container followed by coagulation of the collected blood sample; and centrifuging the blood sample to separate serum and clot according to the specific gravity.

Conventional blood collection containers for collecting blood are made of a glass or a synthetic resin such as polystyrene, polymethyl methacrylate, polyethylene, or polyethylene terephthalate. Blood collection containers made of a glass allow blood to coagulate in a comparatively short time, but still require about 40 to 60 minutes for blood coagulation. In contrast, containers for blood tests made of a synthetic resin require four hours or more for blood coagulation. In order to further reduce the time required for blood to coagulate, blood coagulation promoting agents for promoting blood coagulation have been used.

As is known, blood coagulation is initiated with activation of the blood coagulation factor XII and completed by conversion of fibrinogen to fibrin through a large number of reactions and has a plurality of complex pathways. In Patent Documents 1 to 3, an enzymatic agent (e.g. thrombin or snake venom enzyme) for promoting the conversion reaction of fibrinogen to fibrin at the final stage of blood coagulation is used as a blood coagulation promoting agent for promoting blood coagulation. Use of such an enzymatic agent as a blood coagulation promoting agent allows blood to coagulate within five minutes.

PRIOR ART DOCUMENT

Patent Document

Patent Document 1: JP HEI 10(1998)-260180 A
Patent Document 2: JP 2001-269328 A
Patent Document 3: JP 2002-323488 A

DISCLOSURE OF THE INVENTION

Problem which the Invention is to Solve

Bubbles may be generated by introducing or vacuum sucking blood into a blood collection container. In the case where such a conventional blood coagulation promoting agent as described in Patent Document 1 is used, blood coagulates quickly and simultaneously with generation of bubbles, which often results in formation of bubbly clots containing a bubble. Centrifugation of a blood sample containing bubbly clots that have a small specific gravity may result in contamination of red blood cells in serum caused by contact of bubbly clots with serum. In addition, bubbly clots may inhibit collection of serum separated by centrifugation.

In view of the above-mentioned aspects of the conventional art, an object of the present invention is to provide a blood collection container that allows blood to coagulate in a short time and is capable of preventing formation of bubbly clots caused by coagulation of blood with bubbles contained therein after collection of blood in the blood collection container.

Means of Solving the Problems

The present invention provides a blood collection container housing a blood coagulation promoting agent and an antifoaming agent. The antifoaming agent is a polyoxyalkylene or a derivative thereof, and the amount of the antifoaming agent is $2.0 \times 10^{-3}$ to 0.2 mg per mL of blood to be collected in the blood collection container.

In the present invention, it is preferable that the blood collection container further houses a water-soluble binder. The water-soluble binder allows the blood coagulation promoting agent and the antifoaming agent to more uniformly attach to the inner surface of the blood collection container and prevents the blood coagulation promoting agent and the antifoaming agent from peeling off the inner surface of the blood collection container. Blood flows into the blood collection container, and then contacts and is mixed with the water-soluble binder. Immediately after the contact, the water-soluble binder dissolves in the blood and allows uniform dispersion of the blood coagulation promoting agent in the blood.

The water-soluble binder is preferably at least one species selected from the group consisting of polyvinyl alcohol, polyvinyl pyrrolidone, acrylic acid copolymers, and polyoxyalkylene block copolymers. Use of these water-soluble binders more effectively prevents the blood coagulation promoting agent and the antifoaming agent from peeling off the inner surface of the blood collection container.

In another specific aspect of the present invention, the antifoaming agent is positioned from a first height level to a second height level. The first height level is higher than a liquid level of blood to be collected in the blood collection container, and the second height level is lower than the liquid level of blood. With this structure, the blood collected in the blood collection tube contacts the antifoaming agent. Therefore, bubbles immediately disappear even in the case where bubbles are generated.

In still another specific aspect of the present invention, the blood collection container is provided with a tubular container having an opening at one end and a plug sealingly attached to the opening.

In the present invention, the antifoaming agent is preferably deposited substantially on the entire inner surface of the tubular container. This structure is more effective for removing bubbles.

In the present invention, the blood coagulation promoting agent housed in the blood collection container preferably contains serine protease. Serine protease contained therein further improves coagulation efficiency of blood.

In still another specific aspect of the blood collection container of the present invention, although blood is vacuum collected to directly reach the bottom in the inside of the blood collection container, the blood collection container houses serine protease in an area in which serine protease does not directly contact blood flow. This structure prevents serine protease from contacting blood almost simultaneously with collection of blood, and thereby prevents the blood from coagulating immediately after the blood collection. Accordingly, it is possible to prevent blood from coagulating with bubbles contained therein and to further improve coagulation efficiency of blood without bubbles contained therein.

In the present invention, serine protease is preferably applied to the inner surface of the blood collection container by spray coating. In the case where serine protease is applied by spray coating, collected blood coagulates immediately after contact with serine protease.

In the present invention, it is more preferable that the blood coagulation promoting agent contains an adsorbent inorganic substance. The adsorbent inorganic substance contained therein allows blood to coagulate more immediately after contact with the blood coagulation promoting agent.

In still another specific aspect of the blood collection container of the present invention, the adsorbent inorganic substance is positioned from the first height level to the second height level in the blood collection container. The first height level is higher than a liquid level of blood to be collected in the blood collection container, and the second height level is lower than the liquid level. This structure allows blood collected in the blood collection container to contact the adsorbent inorganic substance, and thereby allows more uniform blood coagulation in a shorter time.

In the present invention, the adsorbent inorganic substance is preferably deposited substantially on the entire inner surface of the tubular container. This structure allows more uniform blood coagulation in a shorter time.

The blood collection container of the present invention is preferably a vacuum blood collection tube, the interior of which is at a reduced pressure. In this case, it is easy to collect a predetermined amount of blood.

Effects of the Invention

In the present invention, owing to the blood coagulation promoting agent housed in the blood collection container, blood is allowed to coagulate in a short time. In addition, owing to a specific amount of the antifoaming agent housed in the blood collection container, which is a polyoxyalkylene or a derivative thereof, bubbles generated in blood collected in the blood collection container sufficiently disappear before coagulation of the blood. Therefore, blood is less likely to coagulate with bubbles contained therein, and thereby bubbly clots are less likely to form. Accordingly, it is possible to prevent contamination of red blood cells in serum during centrifugation. In addition, collection of serum separated by centrifugation is hardly inhibited by the presence of bubbly clots.

BRIEF DESCRIPTION OF THE DRAWINGS

FIGS. 1 (a) and (b) are a perspective view of the external appearance and a front cross-sectional view of a blood collection container according to one embodiment of the present invention, respectively.

BEST MODE FOR CARRYING OUT THE INVENTION

Hereinafter, the present invention is illustrated by describing the specific embodiments of the present invention referring to the figures.

FIGS. 1 (a) and (b) are a perspective view of the external appearance and a front cross-sectional view of a blood collection container according to one embodiment of the present invention.

As shown in FIGS. 1 (a) and (b), a blood collection container 1 for collecting blood is provided with a tubular container 2 and a plug 3. The tubular container 2 has an opening 2a at one end and a bottom 2b at the other end opposite to the one end. The plug 3 has a large diameter part 3a and a small diameter part 3b whose diameter is smaller than that of the large diameter part 3a. The small diameter part 3b of the plug 3 is pressed into the opening 2a of the tubular container 2 so that the plug 3 is attached fluid- and air-tightly.

Examples of the material of the tubular container 2 include thermoplastic resins such as polyethylene, polypropylene, polystyrene, polyethylene terephthalate, polymethyl methacrylate, and polyacrylonitrile; thermosetting resins such as unsaturated polyester resins, epoxy resins, and epoxy acrylate resins; modified natural resins such as cellulose acetate, cellulose propionate, ethyl cellulose, and ethyl chitin; glasses such as silicate glass including soda lime glass, phosphosilicate glass, and borosilicate glass, and silica glass; and any compounds mainly composed of these.

The material and shape of the plug 3 are selected so that the plug 3 is capable of being attached fluid- and air-tightly to the opening 2a of the tubular container 2. The plug 3 is preferably designed to be passed through by a blood collection needle. The plug 3 may be, for example, a rubber plug shaped to fit the opening 2a, a rubber plug having the outer surface covered with a plastic or the like to effectively prevent contact of blood with the human body when the plug 3 is pulled out through the opening 2a after blood collection, or a sheet-shaped sealing member.

Examples of the material of the plug 3 include rubbers such as synthetic resins, elastomers, butyl rubber, and halogenated butyl rubbers, and metal foils such as aluminum foil. Among these, butyl rubber is preferable because of its ability to improve sealing properties.

The blood collection container 1 houses a blood coagulation promoting agent-containing composition 4 and an antifoaming agent-containing composition 5. The blood coagulation promoting agent-containing composition 4 contains a blood coagulation promoting agent (A), which is described later. The antifoaming agent-containing composition 5 contains a blood coagulation promoting agent (B), which is described later, and an antifoaming agent, which is a polyoxyalkylene or a derivative thereof. Namely, the blood collection container 1 houses the blood coagulation promoting agent (A), the blood coagulation promoting agent (B), and the antifoaming agent, which is a polyoxyalkylene or a derivative thereof.

The blood coagulation promoting agent-containing composition 4 is housed in an area to avoid direct contact with blood flow if blood is collected in the blood collection container 1. The blood coagulation promoting agent-containing composition 4 is preferably housed in an area from 7 mm to 50 mm from the opening of the tubular container 2, more preferably 7 mm to 40 mm, and furthermore preferably 7 mm to 30 mm. In this case, the blood coagulation promoting agent (A) hardly contacts blood, for example, when the blood collection container 1 is kept upright. Therefore, bubbles sufficiently disappear before coagulation of blood, thus preventing the blood from coagulating with bubbles contained therein.

The blood coagulation promoting agent-containing composition 4 is applied to the inner surface 2c of the tubular container 2 by spray coating to be almost uniformly attached to the inner surface 2c of the tubular container 2. The blood coagulation promoting agent-containing composition 4 containing the blood coagulation promoting agent (A) is preferably applied by spray coating because more uniform attachment to the inner surface 2c of the tubular container 2 is possible.

Examples of application methods using a spray include: a method in which two fluids of air and an agent solution are sprayed in the aerosol form by the pressure of a compressed gas using a spray nozzle of a double-tube structure; and a method in which drops of an agent solution is sprayed by applying the pressure of a compressed gas using a spray nozzle of a single-tube structure with one or more of fine through holes.

The antifoaming agent-containing composition 5 is deposited from the first height level to the second height level. The first height level is lower than a liquid level of blood to be collected in the blood collection container 1, and the second height level is higher than the liquid level. Namely, if blood is collected in the blood collection container 1, the antifoaming agent-containing composition 5 is housed to contact the blood. In this structure, blood is collected followed by contact with the antifoaming agent. Therefore, bubbles immediately disappear even in the case where bubbles are generated.

The antifoaming agent-containing composition 5 is applied by spray coating substantially to the entire inner surface 2c of the tubular container 2 to be almost uniformly deposited substantially on the entire inner surface 2c of the tubular container 2. The blood coagulation promoting agent (B), which is an adsorbent inorganic substance or the like, and the antifoaming agent, which is a polyoxyalkylene or a derivative thereof, are preferably deposited substantially on the entire inner surface 2c of the tubular container 2. The area defined by the phrase "substantially on the entire inner surface 2c of the tubular container 2" used herein may or may not include the area of the inner surface 2c of the tubular container 2 in contact with the plug 3b attached to the opening 2a of the tubular container 2.

In the blood collection container 1, the antifoaming agent-containing composition 5 is applied to the inner surface 2c of the tubular container 2, and then the blood coagulation promoting agent-containing composition 4 is applied thereto. The blood coagulation promoting agent-containing composition 4 may be applied before the antifoaming agent-containing composition 5 is applied.

The blood coagulation promoting agent (A) in the blood coagulation promoting agent-containing composition 4 is a hydrolase capable of hydrolyzing the bond between arginine and any amino acid residue and/or the bond between lysine and any amino acid residue in peptide chains.

Specific example of the blood coagulation promoting agent (A) include: serine proteases such as trypsin, thrombin, and snake venom thrombin-like enzyme; thiol proteases such as cathepsin B and ficin; and hydrolases such as metal proteases including kininase I. The blood coagulation promoting agent (A) is preferably a serine protease among these and thrombin is preferable among the serine proteases because they improve the coagulation rate of blood.

A too small amount of the blood coagulation promoting agent (A) may cause insufficient coagulation, and a too large amount may adversely affect results of tests. The amount of the blood coagulation promoting agent (A) housed in the blood collection container 1 is preferably 0.5 to 50 units per mL of blood to be collected, and more preferably 1 to 20 units per mL.

The blood coagulation promoting agent-containing composition 4 preferably contains a stabilizer for the blood coagulation promoting agent (A). The blood collection container 1 preferably houses the stabilizer. For example, an enzyme-deactivated product obtained by deactivating the above-described hydrolase used as the blood coagulation promoting agent (A) by radiation irradiation and β-alanine may be used as the stabilizer. Examples of radioactive rays used in the radiation irradiation include gamma rays and electron beams. Any of the enzyme-deactivated products may be used alone, or two or more of these may be used in combination.

The amount of the enzyme-deactivated product in the blood collection container 1 is preferably 0.001 to 100 μg per unit of the blood coagulation promoting agent (A), more preferably 0.01 to 10 μg, and further more preferably 0.03 to 5 μg. A too small amount of the enzyme-deactivated products may fail to sufficiently stabilize the hydrolase, and use of a too large amount thereof is a disadvantage in terms of production cost. The enzyme-deactivated product is preferably used in the minimum amount required to produce desired performance.

The enzyme-deactivated product may be added after deactivation by radiation irradiation, or by adding an active hydrolase and then deactivating portion of the hydrolase by radiation irradiation of the hydrolase.

The amount of β-alanine housed in the blood collection container 1 is preferably 0.01 to 1000 μg per unit of the blood coagulation promoting agent (A), more preferably 0.1 to 200 μg, and most preferably 0.5 to 50 μg. A too small amount of β-alanine may fail to sufficiently stabilize the hydrolase, and a too large amount of β-alanine may not sufficiently dissolve in a solution containing the hydrolase, which may result in nonuniformity of the components of the blood coagulation promoting agent-containing composition 4 or cause a difficulty in applying the blood coagulation promoting agent-containing composition 4 by spray coating. The amount of β-alanine is preferably selected so that β-alanine uniformly dissolves in the hydrolase.

The antifoaming agent in the antifoaming agent-containing composition 5 is a polyoxyalkylene or a derivative thereof. Suitable examples of "a polyoxyalkylene or a derivative thereof" include, but not particularly limited to, substances with low solubility but high dispersibility to water.

"A polyoxyalkylene or a derivative thereof" is preferably a polyoxyalkylene ether because of its excellent antifoaming effect. Examples of a polyoxyalkylene ether include polyoxypropylene, polyoxypropylene glyceryl ether, polyoxyethylene, polyoxyethylene glyceryl ether, polyoxyethylene polyoxypropylene, and polyoxyethylene-polyoxypropylene glyceryl ether.

The amount of the antifoaming agent housed in the blood collection container 1 is within the range of $2.0 \times 10^{-3}$ to 0.2 mg per mL of blood to be collected. A too small amount of the antifoaming agent may fail to produce sufficient antifoaming effect, and a too large amount may cause residual insoluble substances which tend to clog a nozzle for collecting blood, for example, upon blood collection for clinical examinations, and thus may cause troubles in clinical examinations. Therefore, the amount of the antifoaming agent in the blood collection container 1 is preferably within the range of $3.0 \times 10^{-3}$ to 0.11 mg per mL of blood to be collected.

The blood coagulation promoting agent (B) in the antifoaming agent-containing composition 5 is an adsorbent substance. The antifoaming agent-containing composition 5 preferably contains the blood coagulation promoting agent (B), which is an adsorbent substance. The blood collection container 1 preferably houses the blood coagulation promoting agent (B), which is an adsorbent substance.

Examples of the adsorbent substance include silica, glasses, kaolin, celite, and bentonite. Since these adsorbent inorganic substances have a large specific surface area, use of such an adsorbent inorganic substance as the blood coagulation promoting agent (B) allows blood to more uniformly coagulate in a shorter time by allowing blood to contact the adsorbent inorganic substance. The blood coagulation promoting agent (B) is preferably in the powder form with a larger specific surface area which allows blood to further more uniformly coagulate in a further shorter time.

A too small amount of the blood coagulation promoting agent (B) may make the coagulation time of blood longer, possibly resulting in insufficient coagulation, and a too large amount may adversely affect results of tests. Therefore, the amount of the blood coagulation promoting agent (B) housed in the blood collection container 1 is preferably $1 \times 10^{-6}$ to $1 \times 10^{-2}$ g per mL of blood to be collected, and more preferably $1 \times 10^{-5}$ to $1 \times 10^{-3}$ g.

Both of the blood coagulation promoting agent-containing composition 4 and the antifoaming agent-containing composition 5 preferably contain a water-soluble binder. The blood collection container 1 preferably houses the water-soluble binder. Use of the water-soluble binder allows the blood coagulation promoting agent and the antifoaming agent to more uniformly attach to the inner surface of the blood collection container 1 and prevents the blood coagulation promoting agent and the antifoaming agent from peeling off the inner surface of the blood collection container 1. Blood flows into the blood collection container 1, and then contacts and is mixed with the water-soluble binder. Immediately after the contact, the water-soluble binder is dissolved and uniformly dispersed therein.

The water-soluble binder is not particularly limited and may be any compound that does not affect tests. Examples thereof include polyvinyl alcohol, polyvinyl pyrrolidone, acrylic acid copolymers, and polyoxyalkylene block copolymers. Among these, polyvinyl pyrrolidone is more preferable because it more effectively prevents the blood coagulation promoting agent and the antifoaming agent from peeling off the inner surface of the blood collection container 1.

The weight average molecular weight of polyvinyl pyrrolidone is preferably 10,000 to 600,000, and more preferably 30,000 to 500,000. A too low weight average molecular weight tends to cause hemolysis, and a too high weight average molecular weight leads to insufficient solubility to blood, possibly resulting in inhibition of the effects of the hydrolase.

A too small amount of the water-soluble binder may cause the blood coagulation promoting agent and the antifoaming agent to peel off the inner surface of the blood collection container 1, and a too large amount may affect results of tests and inhibit the effects of the hydrolase due to insufficient solubility to blood. Therefore, the amount of water-soluble binder added to the antifoaming agent-containing composition 5 to be housed in the blood collection container 1 is preferably $1 \times 10^{-4}$ to 2 mg per mL of blood to be collected, and more preferably $1 \times 10^{-3}$ to 1 mg. The amount of the water-soluble binder added to the blood coagulation promoting agent-containing composition 4 to be housed in the blood collection container 1 is preferably $1 \times 10^{-4}$ to 2 mg per mL of blood to be collected, and more preferably $1 \times 10^{-3}$ to 1 mg. The total amount of the water-soluble binder housed in the blood collection container 1 is preferably $2 \times 10^{-4}$ to 4 mg per mL of blood to be collected, and more preferably $2 \times 10^{-3}$ to 2 mg.

The blood collection container 1 houses a serum separating agent 6 at the bottom 2b. The blood collection container 1 preferably houses the serum separating agent 6, as described above. The blood separating agent 6 housed in the blood collection container 1 moves to be placed between clots and serum during centrifugation to form a partition. Thus, serum is effectively separated.

The serum separating agent 6 is a thixotropic substance in the gel form, and may be obtained, for example, by adding additives such as thixotropy-imparting agents, specific-gravity-controlling agents, compatibilizing agents, or viscosity modifiers to a synthetic resin or the like which is flowable at ambient temperature, and mixing them. Alternatively, a plasticizer may be added to a resin which is a solid at ambient temperature to provide flowability, and then additives such as thixotropy-imparting agents, specific-gravity-controlling agents, compatibilizing agents, or viscosity modifiers may be added.

Examples of the synthetic resin include oligomers of dicyclopentadiene. Examples of the thixotropy-imparting agents include condensation products of sorbitol and an aromatic aldehyde, and polyoxyethylene/polyoxyalkylene block copolymers. Examples of the specific-gravity-controlling agents include silica. Examples of the viscosity modifiers and plasticizers include phthalate esters, and trimellitic acid esters. Examples of the compatibilizing agents include partially hydrogenated terphenyl.

Although the blood collection container 1 houses the antifoaming agent mixed with the blood coagulation promoting agent (B), the blood coagulation promoting agent (B) and the antifoaming agent may be separated, and for example, each of them may be supported on a carrier. Alternatively, the antifoaming agent may be added to the blood coagulation promoting agent-containing composition 4, and mixed with the blood coagulation promoting agent (A). The blood coagulation promoting agent and the antifoaming agent may be housed in the blood collection container 1 and mixed at the time of use.

Examples of a method for supporting them on a carrier include a supporting method including applying an aqueous solution or a water dispersion of all the components or each component to be housed in the blood collection container 1 by spray coating, and a supporting method including immersing a carrier to the aqueous solution or the water dispersion.

The blood collection container 1 may be manufactured by any method, and for example, by applying the blood coagulation promoting agent-containing composition 4 and the antifoaming agent-containing composition 5 separately to the inner surface 2c of the tubular container 2, for example, using a spray, and sealingly attaching the plug 3 to the opening 2a of the tubular container 2. The interior of the blood collection container 1 is preferably at a reduced pressure. In this case, the blood collection container 1 can be used as a vacuum blood collection tube.

Hereinafter, the present invention is described in more detail by way of examples. However, the present invention is not limited only to these examples.

The following reagents and the container were used to form blood collection container in Examples and Comparative Examples.

Blood coagulation promoting agent (A): thrombin (trade name: Thrombin (from Bovine Plasma), products of ILS INC.)

Blood coagulation promoting agent (B): silica (trade name: IMSIL A-25, products of UNIMIN SPECIALTY MINERALS)

Antifoaming Agent:
polyoxypropylene glyceryl ether (ADEKA POLYETHER G-4000, available from ADEKA Corporation)
polyoxyethylene polyoxypropylene glyceryl ether (ADEKA POLYETHER AM-502, available from ADEKA Corporation)
polyoxypropylene ether (ADEKA POLYETHER P-3000, available from ADEKA Corporation)

Water-soluble binder: polyvinyl pyrrolidone (PVP-K30, available from Wako Pure Chemical Industries, Ltd.)

Tubular container: tubular container made of polyethylene terephthalate (internal volume 7.8 mL, inner diameter 10.8 mm×length 100 mm, available from Sekisui Chemical Co., Ltd.)

Serum separating agent: thixotropic separating agent (available from Sekisui Chemical Co., Ltd.)

Plug: plug made of butyl rubber

Example 1

The bottom of the tubular container was filled with 0.8 mL of the thixotropic separating agent (serum separating agent). Subsequently, polyoxypropylene glyceryl ether (antifoaming agent) in an amount of $2.0 \times 10^{-3}$ mg per mL of blood was dissolved in an injection solvent to provide a solution, and then polyvinyl pyrrolidone (water-soluble binder) in an amount of 0.088 mg per mL of blood was dissolved in the obtained solution. Next, silica (blood coagulation promoting agent (B)) in an amount of 0.11 mg per mL of blood was further added to the solution and dispersed to provide an antifoaming agent-containing composition. The obtained antifoaming agent-containing composition was uniformly sprayed to the entire internal surface of the tubular container and air-dried.

Then, thrombin (blood coagulation promoting agent (A) was dissolved in polyvinyl pyrrolidone (water-soluble binder, 0.008 mg per mL of blood) to provide a blood coagulation promoting agent-containing composition. The obtained blood coagulation promoting agent-containing composition was uniformly applied by spray coating to the area from 7 to 30 mm from the opening of the tubular container in a thrombin amount of 9.5 units per mL of blood.

The plug was sealingly attached to the opening of the tubular container. The pressure in the inside was reduced to provide a vacuum blood collection tube whose blood collection amount is 5 mL.

Examples 2 to 15

A vacuum blood collection tube was produced in the same manner as in Example 1, except that the antifoaming agent and its amount were changed as shown in Table 1.

Examples 16 to 19

A vacuum blood collection tube was produced in the same manner as in Example 4, except that the amount of the water-soluble binder in the antifoaming agent-containing composition was changed as shown in Table 1.

Examples 20 to 23

A vacuum blood collection tube was produced in the same manner as in Example 4, except that the amount of the blood coagulation promoting agent (A) was changed as shown Table 1.

Example 24

A vacuum blood collection tube was obtained in the same manner as in Example 4, except that the blood coagulation promoting agent-containing composition was uniformly applied to the entire inner surface of the tubular container by spray coating.

Examples 25, 26

A vacuum blood collection tube was produced in the same manner as in Example 24, except that the antifoaming agent was changed as shown in Table 1.

Example 27

A vacuum blood collection tube was produced in the same manner as in Example 4, except that the water-soluble binder was not added to the antifoaming agent-containing composition.

Example 28

A vacuum blood collection tube was produced in the same manner as in Example 4, except that the amount of the water-soluble binder in the antifoaming agent-containing composition was changed as shown in Table 1.

Examples 29, 30

A vacuum blood collection tube was produced in the same manner as in Example 4, except that the amount of the blood coagulation promoting agent (A) was changed as shown in Table 1.

Example 31

A vacuum blood collection tube was produced in the same manner as in Example 4, except that the blood coagulation promoting agent-containing composition was uniformly applied to the area from 7 to 40 mm from the opening of the tubular tube on the inner surface of the tubular container by spray coating.

Example 32

A vacuum blood collection tube was produced in the same manner as in Example 4, except that the blood coagulation promoting agent-containing composition was uniformly applied to the area from 7 to 50 mm from the opening of the tubular tube on the inner surface of the tubular container by spray coating.

Comparative Examples 1 to 3

A vacuum blood collection tube was produced in the same manner as in Example 1, except that the antifoaming agent and its amount were changed as shown in Table 1.

Comparative Example 4

A vacuum blood collection tube was produced in the same manner as in Example 1, except that the antifoaming agent and the blood coagulation promoting agent (B) were not used.

Comparative Example 5

A vacuum blood collection tube was produced in the same manner as in Example 24, except that the antifoaming agent was not used.

Comparative Example 6

A vacuum blood collection tube was produced in the same manner as in Example 24, except that the antifoaming agent and the blood coagulation promoting agent (B) were not used.

Comparative Example 7

A vacuum blood collection tube was produced in the same manner as in Example 1, except that the antifoaming agent was not used.

(Evaluation)

Human fresh blood was vacuum sucked into the tubular container of each blood collection tube with the plug oriented upward. Subsequently, the vacuum blood collection tube was tumbled for five times over five seconds to mix the components and left standing for five minutes. Then, the vacuum blood collection tube was subjected to centrifugation, and assessed using 30 evaluation samples for generation frequencies of bubbly clots and fibrin precipitation (delayed fibrin) caused by insufficient coagulation. In addition, 5% BSA (bovine serum albumin) solution was sucked into each vacuum blood collection tube, and then the level of bubbles was measured after five seconds to evaluate the residual amount of bubbles.

Blood coagulation time was evaluated by measuring the time from suction of blood until blood coagulation was visually observed. Furthermore, each vacuum blood collection tube was assessed for the presence of peeling off of the blood coagulation promoting agent-containing composition (agent) and the antifoaming agent-containing composition (agent) from the inner surface of the tubular container. Evaluation of the presence of floating matter on the surface of the serum separated by centrifugation was also carried out.

Table 1 shows the results.

TABLE 1

| | Antifoaming Agent-Containing Composition | | | | | Blood Coagulation Promoting Agent-Containing Composition | | |
|---|---|---|---|---|---|---|---|---|
| | Antifoaming Agent | | | Blood Coagulation Promoting Agent(B) | Water-Soluble Binder | Blood Coagulation Promoting Agent(A) | Water-Soluble Binder | |
| | Amount of G4000 (mg/mL of Blood) | Amount of AM502 (mg/mL of Blood) | Amount of P3000 (mg/mL of Blood) | Amount of Silica (mg/mL of Blood) | Amount of PVP-K30 (mg/mL of Blood) | Amount of Thrombin (U/mL of Blood) | Amount of PVP-K30 (mg/mL of Blood) | Coated Area |
| Ex. 1 | $2.0 \times 10^{-3}$ | — | — | 0.11 | 0.088 | 9.5 | 0.008 | 7-30 mm |
| Ex. 2 | $3.0 \times 10^{-3}$ | — | — | 0.11 | 0.088 | 9.5 | 0.008 | 7-30 mm |
| Ex. 3 | $4.0 \times 10^{-2}$ | — | — | 0.11 | 0.088 | 9.5 | 0.008 | 7-30 mm |
| Ex. 4 | 0.11 | — | — | 0.11 | 0.088 | 9.5 | 0.008 | 7-30 mm |
| Ex. 5 | 0.2 | — | — | 0.11 | 0.088 | 9.5 | 0.008 | 7-30 mm |
| Ex. 6 | — | $2.0 \times 10^{-3}$ | — | 0.11 | 0.088 | 9.5 | 0.008 | 7-30 mm |
| Ex. 7 | — | $3.0 \times 10^{-3}$ | — | 0.11 | 0.088 | 9.5 | 0.008 | 7-30 mm |
| Ex. 8 | — | $4.0 \times 10^{-2}$ | — | 0.11 | 0.088 | 9.5 | 0.008 | 7-30 mm |
| Ex. 9 | — | 0.11 | — | 0.11 | 0.088 | 9.5 | 0.008 | 7-30 mm |
| Ex. 10 | — | 0.2 | — | 0.11 | 0.088 | 9.5 | 0.008 | 7-30 mm |
| Ex. 11 | — | — | $2.0 \times 10^{-3}$ | 0.11 | 0.088 | 9.5 | 0.008 | 7-30 mm |
| Ex. 12 | — | — | $3.0 \times 10^{-3}$ | 0.11 | 0.088 | 9.5 | 0.008 | 7-30 mm |
| Ex. 13 | — | — | $4.0 \times 10^{-2}$ | 0.11 | 0.088 | 9.5 | 0.008 | 7-30 mm |
| Ex. 14 | — | — | 0.11 | 0.11 | 0.088 | 9.5 | 0.008 | 7-30 mm |
| Ex. 15 | — | — | 0.2 | 0.11 | 0.088 | 9.5 | 0.008 | 7-30 mm |
| Ex. 16 | 0.11 | — | — | 0.11 | $1 \times 10^{-4}$ | 9.5 | 0.008 | 7-30 mm |
| Ex. 17 | 0.11 | — | — | 0.11 | $1 \times 10^{-3}$ | 9.5 | 0.008 | 7-30 mm |
| Ex. 18 | 0.11 | — | — | 0.11 | 1 | 9.5 | 0.008 | 7-30 mm |
| Ex. 19 | 0.11 | — | — | 0.11 | 2 | 9.5 | 0.008 | 7-30 mm |
| Ex. 20 | 0.11 | — | — | 0.11 | 0.088 | 0.5 | 0.008 | 7-30 mm |
| Ex. 21 | 0.11 | — | — | 0.11 | 0.088 | 1 | 0.008 | 7-30 mm |
| Ex. 22 | 0.11 | — | — | 0.11 | 0.088 | 20 | 0.008 | 7-30 mm |
| Ex. 23 | 0.11 | — | — | 0.11 | 0.088 | 50 | 0.008 | 7-30 mm |
| Ex. 24 | 0.11 | — | — | 0.11 | 0.088 | 9.5 | 0.008 | Entire Surface |
| Ex. 25 | — | 0.11 | — | 0.11 | 0.088 | 9.5 | 0.008 | Entire Surface |
| Ex. 26 | — | — | 0.11 | 0.11 | 0.088 | 9.5 | 0.008 | Entire Surface |
| Ex. 27 | 0.11 | — | — | 0.11 | — | 9.5 | 0.008 | 7-30 mm |
| Ex. 28 | 0.11 | — | — | 0.11 | 5 | 9.5 | 0.008 | 7-30 mm |
| Ex. 29 | 0.11 | — | — | 0.11 | 0.088 | 0.1 | 0.008 | 7-30 mm |
| Ex. 30 | 0.11 | — | — | 0.11 | 0.088 | 100 | 0.008 | 7-30 mm |
| Ex. 31 | 0.11 | — | — | 0.11 | 0.088 | 9.5 | 0.008 | 7-40 mm |
| Ex. 32 | 0.11 | — | — | 0.11 | 0.088 | 9.5 | 0.008 | 7-50 mm |
| Comp. Ex. 1 | 0.25 | — | — | 0.11 | 0.088 | 9.5 | 0.008 | 7-30 mm |
| Comp. Ex. 2 | — | 0.25 | — | 0.11 | 0.088 | 9.5 | 0.008 | 7-30 mm |
| Comp. Ex. 3 | — | — | 0.25 | 0.11 | 0.088 | 9.5 | 0.008 | 7-30 mm |
| Comp. Ex. 4 | — | — | — | — | 0.088 | 9.5 | 0.008 | 7-30 mm |

TABLE 1-continued

| | | | | | | | | |
|---|---|---|---|---|---|---|---|---|
| Comp. Ex. 5 | — | — | — | 0.11 | 0.088 | 9.5 | 0.008 | Entire Surface |
| Comp. Ex. 6 | — | — | — | — | 0.088 | 9.5 | 0.008 | Entire Surface |
| Comp. Ex. 7 | — | — | — | 0.11 | 0.088 | 9.5 | 0.008 | 7-30 mm |

| | Evaluation | | | | | |
|---|---|---|---|---|---|---|
| | Bubbly-Clot Generation Frequency (%, n = 30) | Antifoaming Effect Bubble Height (mm) | Delayed-Fibrin Generation Frequency (%) | Coagulation Time (second) | Peeling Off of Agent | Floating Matter |
| Ex. 1 | 3 | 8.4 | 0 | 60 | Not Observed | Not Observed |
| Ex. 2 | 0 | 5.3 | 0 | 60 | Not Observed | Not Observed |
| Ex. 3 | 0 | 2.2 | 0 | 60 | Not Observed | Not Observed |
| Ex. 4 | 0 | 2.2 | 0 | 60 | Not Observed | Not Observed |
| Ex. 5 | 0 | 1.8 | 0 | 60 | Not Observed | Slightly Observed |
| Ex. 6 | 0 | 6.3 | 0 | 60 | Not Observed | Not Observed |
| Ex. 7 | 0 | 6.2 | 0 | 60 | Not Observed | Not Observed |
| Ex. 8 | 0 | 1.7 | 0 | 60 | Not Observed | Not Observed |
| Ex. 9 | 0 | 0.9 | 0 | 60 | Not Observed | Not Observed |
| Ex. 10 | 0 | 0.5 | 0 | 60 | Not Observed | Slightly Observed |
| Ex. 11 | 7 | 10.8 | 0 | 60 | Not Observed | Not Observed |
| Ex. 12 | 0 | 7.6 | 0 | 60 | Not Observed | Not Observed |
| Ex. 13 | 0 | 5.0 | 0 | 60 | Not Observed | Not Observed |
| Ex. 14 | 0 | 3.6 | 0 | 60 | Not Observed | Not Observed |
| Ex. 15 | 0 | 3.1 | 0 | 60 | Not Observed | Slightly Observed |
| Ex. 16 | 0 | 2.0 | 0 | 60 | Slightly Observed | Not Observed |
| Ex. 17 | 0 | 1.8 | 0 | 60 | Not Observed | Not Observed |
| Ex. 18 | 0 | 2.5 | 0 | 60 | Not Observed | Not Observed |
| Ex. 19 | 0 | 2.9 | 0 | 70 | Not Observed | Not Observed |
| Ex. 20 | 0 | 2.1 | 0 | 100 | Not Observed | Not Observed |
| Ex. 21 | 0 | 2.1 | 0 | 50 | Not Observed | Not Observed |
| Ex. 22 | 0 | 2.3 | 0 | 60 | Not Observed | Not Observed |
| Ex. 23 | 0 | 1.8 | 0 | 40 | Not Observed | Not Observed |
| Ex. 24 | 20 | 2.4 | 0 | 60 | Not Observed | Not Observed |
| Ex. 25 | 20 | 1.1 | 0 | 60 | Not Observed | Not Observed |
| Ex. 26 | 30 | 3.4 | 0 | 60 | Not Observed | Not Observed |
| Ex. 27 | 0 | 3.5 | 0 | 80 | Observed | Not Observed |
| Ex. 28 | 0 | 8.9 | 0 | 120 | Not Observed | Not Observed |
| Ex. 29 | 0 | 2.3 | 0 | 120 | Not Observed | Not Observed |
| Ex. 30 | 0 | 2.1 | 0 | 30 | Not Observed | Not Observed |
| Ex. 31 | 3 | 2.5 | 0 | 60 | Not Observed | Not Observed |
| Ex. 32 | 7 | 1.6 | 0 | 60 | Not Observed | Not Observed |
| Comp. Ex. 1 | 0 | 1.5 | 0 | 60 | Not Observed | Observed |
| Comp. Ex. 2 | 0 | 0.2 | 0 | 60 | Not Observed | Observed |
| Comp. Ex. 3 | 0 | 3.1 | 0 | 60 | Not Observed | Observed |
| Comp. Ex. 4 | 13 | 31.2 | 80 | 120 | Not Observed | Not Observed |
| Comp. Ex. 5 | 70 | 31.6 | 0 | 60 | Not Observed | Not Observed |
| Comp. Ex. 6 | 70 | 31.6 | 10 | 90 | Not Observed | Not Observed |
| Comp. Ex. 7 | 17 | 28.7 | 0 | 60 | Not Observed | Not Observed |

In the vacuum blood collection tubes of Examples 1, 6, 11 in which the antifoaming agent was used in an amount of $2.0 \times 10^{-3}$ mg per mL of blood, portion of bubbles did not disappear and remained although their antifoaming effect was better than that of Comparative Example 7 in which the antifoaming agent was not used. Their bubbly-clot generation frequencies were lower than that of Comparative Example 7 in which the antifoaming agent was not used. The vacuum blood collection containers of Examples 5, 10, 15 in which 0.2 mg of the antifoaming agent was used per mL of blood were excellent in antifoaming effect. However, in these vacuum blood collection containers, floating matter caused due to their high antifoaming agent concentrations was slightly observed on the surface of the serums separated by centrifugation although the amount of the floating matter was not at a level that affects results of tests. In the vacuum blood collection tubes of Example 2 to 4, 7 to 9, and 12 to 14 in which the antifoaming agent was used in an amount of $3 \times 10^{-3}$ to 0.11 mg per mL of blood, no floating matter was observed. In addition, all of them were excellent in antifoaming effect, and formation of bubbly clots was not observed.

The vacuum blood collection tubes of Comparative Examples 1 to 3 in which 0.25 mg/mL of the antifoaming agent was used per mL of blood were excellent in antifoaming effect. However, since their antifoaming agent concentrations were high, a large amount of floating matter was observed on the surface of the serums separated by centrifugation. Considering these results, the amount of the antifoaming agent is preferably $3 \times 10^{-3}$ to 0.11 mg per mL of blood to be collected.

In the vacuum blood collection tube of Comparative Example 7 in which the antifoaming agent was not used, bubbles did not disappear after blood collection. However, since the blood coagulation promoting agent (A) was applied to the area in which the blood coagulation promoting agent (A) does not directly contact blood flow, the bubbly-clot generation frequency was lower than that of the vacuum blood collection tube of Comparative Example 6 in which the blood coagulation promoting agent (A) was applied to the entire inner surface of the tubular container.

In the vacuum blood collection tubes of Examples 16 to 19 in which to the antifoaming agent-containing composition was added the water-soluble binder in an amount of $1 \times 10^{-4}$ to 2 mg per mL of blood, no bubbly clots were generated, and no floating matter was observed. In the vacuum blood collection tube of Example 27 in which the water-soluble binder was not added to the antifoaming agent-containing composition, the agents peeled off the inner surface of the tubular container. In addition, the blood coagulation promoting agent was not uniformly dispersed in blood, and thereby nonuniformly coagulated. In the vacuum blood collection tube of Example 28 in which to the antifoaming agent-containing composition was added the water-soluble binder in an amount of 5 mg per mL of blood, the dissolution rate of the blood coagulation promoting agent was slow, and thereby the coagulation time was long. In addition, this vacuum blood collection tube may cause an influence on results of tests. Considering these results, it is preferable that the water-soluble binder is added to the antifoaming agent-containing composition. The amount of the water-soluble binder in the antifoaming agent-containing composition is preferably $1 \times 10^{-4}$ to 2 mg per mL of blood to be collected, and more preferably $1 \times 10^{-3}$ to 1 mg.

In the vacuum blood collection tubes of Examples 20 to 23 in which the blood coagulation promoting agent (A) was used in an amount of 0.5 to 50 units per mL of blood, no bubbly clots were generated, and no floating matter was observed. However, the vacuum blood collection tube of Example 29 in which the blood coagulation promoting agent (A) was used in an amount of 0.1 units per mL of blood required a long coagulation time. On the other hand, the vacuum blood collection tube of Example 30 in which the blood coagulation promoting agent (A) was used in an amount of 100 units per mL of blood had no functional problems but may cause an influence on results of tests. In addition, this blood collection tube is not suitable as an industrial product due to its high cost. Considering these results, the amount of the blood coagulation promoting agent (A) is preferably 0.5 to 50 units per mL of blood to be collected, and more preferably 1 to 20 units.

In Examples 31 and 32 in which the area to which the blood coagulation promoting agent (A) was applied was changed, no floating matter was observed. In addition, both of them were excellent in antifoaming effect, and their bubbly-clot generation frequencies were low. Therefore, the blood coagulation promoting agent-containing composition 4 is preferably housed in the area from 7 mm to mm, more preferably from 7 mm to 40 mm, and most preferably from 7 mm to 30 mm from the opening of the tubular container 2.

In the vacuum blood collection tube of Comparative Example 4 in which the antifoaming agent and the blood coagulation promoting agent (B) were used, bubbles did not disappear after blood collection. However, since the blood coagulation promoting agent (A) was applied to the area in which the blood coagulation promoting agent (A) does not directly contact blood flow, its bubbly-clot generation frequency was lower than that of the vacuum blood collection tube of Comparative Example 6 in which the blood coagulation promoting agent (A) was applied the entire inner surface of the tubular container. However, blood insufficiently coagulated due to lack of the blood coagulation promoting agent (B), and the delayed-fibrin generation frequency was high.

In the vacuum blood collection tubes of Examples 24 to 26 in which the blood coagulation promoting agent (A) was applied the entire inner surface of the tubular container, blood coagulated before disappearance of bubbles. Therefore, the generation frequencies of bubbly clots in the analytes separated by centrifugation were high, but still lower than that of the vacuum blood collection tube of Comparative Example 5 in which the antifoaming agent was not used.

The coagulation time of the vacuum blood collection tube of Comparative Example 5 in which the blood coagulation promoting agent (A) was applied to the entire inner surface of the tubular container and the antifoaming agent was not used was short, but the bubbly-clot generation frequency in the analytes separated by centrifugation was high.

Considering these results, in order to reduce the bubbly-clot generation frequency, the blood coagulation promoting agent (A) is preferably housed in an area in which the blood coagulation promoting agent (A) does not directly contact blood flow. In addition, since addition of the blood coagulation promoting agent (B) allows reduction in the coagulation time of blood and uniform coagulation, the blood collection container preferably houses the blood coagulation promoting agent (B).

EXPLANATION OF SYMBOLS

1 Blood collection container
2 Tubular container
2a Opening
2b Bottom
2c Inner surface
3 Plug
3a Large diameter part
3b Small diameter part
4 Blood coagulation promoting agent-containing composition
5 Antifoaming agent-containing composition
6 Serum separating agent

The invention claimed is:

1. A blood collection container comprising:
   a tubular container having an opening at one end and a bottom at the other end opposite to the one end and
   a blood coagulation promoting agent (A) being a hydrolase capable of hydrolyzing the bond between arginine and any amino acid residue and/or the bond between lysine and any amino acid residue in peptide chains; and
   an anti foaming agent,
   said antifoaming agent being a polyoxyalkylene or a derivative thereof,
   wherein the amount of said antifoaming agent is $2.0 \times 10^{-3}$ to 0.2 mg per mL of blood to be collected in the blood collection container, and a blood coagulation promoting agent-containing composition comprising said blood coagulation promoting agent (A) and an antifoaming agent-containing composition comprising said antifoaming agent are housed in said tubular container so that a lowermost portion of said blood coagulation promoting agent-containing composition with respect to said bottom of the tubular container is located nearer to the opening end as compared to a lowermost portion of said antifoaming agent-containing composition with respect to said bottom of the tubular container.

2. The blood collection container according to claim 1, further comprising a water-soluble binder.

3. The blood collection container according to claim 2, wherein said water-soluble binder is at least one selected from the group consisting of polyvinyl alcohol, polyvinyl pyrrolidone, acrylic acid copolymers, and polyoxyalkylene block copolymers.

4. The blood collection container according to claim 1, further comprising
   a tubular container having an opening at one end and a plug sealingly attached to said opening.

5. The blood collection container according to claim 4, wherein said antifoaming agent is deposited substantially on an entire inner surface of said tubular container.

6. The blood collection container according to claim 1, wherein said hydrolase is serine protease.

7. The blood collection container according to claim 6, wherein said serine protease is applied to the inner surface of the blood collection container by spray coating.

8. The blood collection container according to claim 1, further comprising a blood coagulation promoting agent (B) which comprises an adsorbent inorganic substance.

9. The blood collection container according to claim 8, wherein said blood coagulation promoting agent (B) is deposited substantially on the entire inner surface of said tubular container.

10. The blood collection container according to claim 1, which is a vacuum blood collection tube, the interior of which is at a reduced pressure.

11. The blood collection container according to claim 8, wherein said antifoaming agent-containing composition further comprises said blood coagulation promoting agent (B).

12. The blood collection container according to claim 2, which is a vacuum blood collection tube, the interior of which is at a reduced pressure.

13. The blood collection container according to claim 3, which is a vacuum blood collection tube, the interior of which is at a reduced pressure.

14. The blood collection container according to claim 4, which is a vacuum blood collection tube, the interior of which is at a reduced pressure.

15. The blood collection container according to claim 6, which is a vacuum blood collection tube, the interior of which is at a reduced pressure.

16. The blood collection container according to claim 8, which is a vacuum blood collection tube, the interior of which is at a reduced pressure.

17. The blood collection container according to claim 11, wherein said blood coagulation promoting agent (B) is deposited substantially on the entire inner surface of said tubular container.

18. The blood collection container according to claim 4, comprising
said blood coagulation promoting agent (A) is housed in an area from 7 mm to 50 mm from the opening of said tubular container.

* * * * *